(12) United States Patent
Stopek et al.

(10) Patent No.: US 9,572,907 B2
(45) Date of Patent: Feb. 21, 2017

(54) IMPLANTABLE POLYMERIC FILMS

(75) Inventors: Joshua Stopek, Guilford, CT (US); Amin Elachchabi, Hamden, CT (US)

(73) Assignee: Covidien LP, Mansfield, MA (US)

(*) Notice: Subject to any disclaimer, the term of this patent is extended or adjusted under 35 U.S.C. 154(b) by 70 days.

(21) Appl. No.: 12/896,118

(22) Filed: Oct. 1, 2010

(65) Prior Publication Data
US 2012/0082712 A1 Apr. 5, 2012

(51) Int. Cl.
| | | |
|---|---|---|
| *A61L 17/14* | (2006.01) | |
| *A61L 17/00* | (2006.01) | |
| *A61L 31/10* | (2006.01) | |
| *A61L 31/16* | (2006.01) | |
| *A61L 27/34* | (2006.01) | |
| *A61L 27/50* | (2006.01) | |
| *A61L 31/14* | (2006.01) | |
| *A61F 2/00* | (2006.01) | |

(52) U.S. Cl.
CPC ............ *A61L 17/145* (2013.01); *A61L 17/005* (2013.01); *A61L 27/34* (2013.01); *A61L 27/502* (2013.01); *A61L 31/10* (2013.01); *A61L 31/141* (2013.01); *A61L 31/16* (2013.01); *A61F 2/0063* (2013.01)

(58) Field of Classification Search
USPC ........................................................ 424/423
See application file for complete search history.

(56) References Cited

U.S. PATENT DOCUMENTS

| | | | |
|---|---|---|---|
| 3,887,699 A | | 6/1975 | Yolles |
| 4,572,906 A | * | 2/1986 | Sparkes et al. ............... 424/445 |
| 4,767,628 A | | 8/1988 | Hutchinson |
| 5,108,424 A | | 4/1992 | Hoffman, Jr. et al. |
| 6,264,702 B1 | | 7/2001 | Ory et al. |
| 6,270,792 B1 | | 8/2001 | Guillemet et al. |
| 6,500,777 B1 | | 12/2002 | Wiseman et al. |
| 7,041,868 B2 | | 5/2006 | Greene et al. |
| 7,252,837 B2 | | 8/2007 | Guo et al. |
| 7,279,177 B2 | | 10/2007 | Looney et al. |
| 7,556,598 B2 | | 7/2009 | Rao |
| 2002/0098155 A1 | * | 7/2002 | Dodd ........................ A61K 8/21 424/49 |
| 2002/0131988 A1 | | 9/2002 | Foster et al. |
| 2004/0018241 A1 | * | 1/2004 | Houze et al. ................. 424/486 |
| 2004/0098118 A1 | | 5/2004 | Granada et al. |
| 2004/0224007 A1 | | 11/2004 | Zhang |
| 2005/0244455 A1 | | 11/2005 | Greenawalt |
| 2005/0261782 A1 | | 11/2005 | Hoganson |
| 2006/0034887 A1 | | 2/2006 | Pelissier |
| 2006/0116696 A1 | | 6/2006 | Odermatt et al. |
| 2006/0121078 A1 | | 6/2006 | Trogolo et al. |
| 2006/0188546 A1 | | 8/2006 | Giroux |
| 2006/0224038 A1 | | 10/2006 | Rao |
| 2007/0098779 A1 | * | 5/2007 | Hanzen et al. ............... 424/451 |
| 2007/0129736 A1 | | 6/2007 | Solecki |
| 2007/0198040 A1 | | 8/2007 | Buevich et al. |
| 2007/0244548 A1 | | 10/2007 | Myers et al. |
| 2008/0109017 A1 | | 5/2008 | Herweck et al. |
| 2008/0113001 A1 | | 5/2008 | Herweck et al. |
| 2008/0118550 A1 | | 5/2008 | Martakos et al. |
| 2008/0199506 A1 | | 8/2008 | Horres et al. |
| 2009/0036996 A1 | | 2/2009 | Roeber |
| 2009/0092651 A1 | | 4/2009 | Shah et al. |
| 2009/0142385 A1 | * | 6/2009 | Gross et al. .................. 424/422 |
| 2009/0163936 A1 | | 6/2009 | Yang et al. |
| 2010/0003308 A1 | | 1/2010 | Tapolsky et al. |
| 2010/0089409 A1 | | 4/2010 | Bertagnoli |

FOREIGN PATENT DOCUMENTS

| | | |
|---|---|---|
| FR | 2 857 851 A1 | 1/2005 |
| JP | 600203264 | 10/1985 |
| JP | 2009502364 A | 1/2009 |
| WO | 93/11805 | 6/1993 |
| WO | 9640302 A1 | 12/1996 |
| WO | WO 02/34304 | 5/2002 |
| WO | WO 2006/020922 A2 | 2/2006 |
| WO | WO 2006/036967 | 4/2006 |
| WO | 2010042798 A2 | 4/2010 |
| WO | WO 2010/093333 A1 | 8/2010 |

OTHER PUBLICATIONS

Cohen et al., Dis Colon Rectum. Jun. 2005; 48(6):1130-9.*
European Search Report for EP 11250641.5-2320 (3 pages).
European Search Report, Application No. EP 11 25 0786 dated Aug. 1, 2014.
Japanese Office Action, Application No. 2011-161080 dated Apr. 22, 2015.

* cited by examiner

*Primary Examiner* — Michael G Hartley
*Assistant Examiner* — Robert Cabral

(57) ABSTRACT

The present disclosure relates to implantable medical devices containing a polymeric film layer containing glycerol and at least one biopolymer.

6 Claims, 17 Drawing Sheets

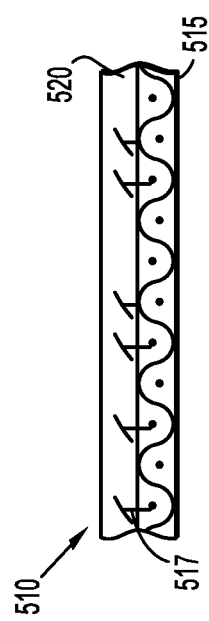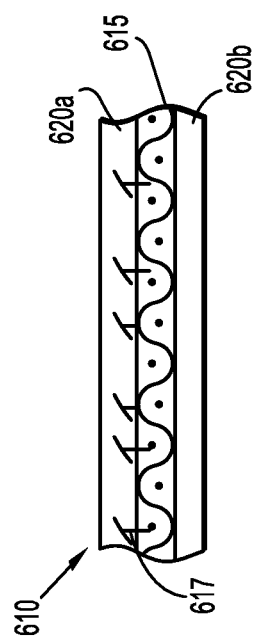

IMPLANTABLE POLYMERIC FILMS

BACKGROUND

Technical Field

The present disclosure relates to implantable medical devices, and more particularly, to implantable medical devices including at least one polymeric film layer made from a mixture of glycerol and a biopolymer.

Background of Related Art

A variety of medical conditions may be treated, at least in part, by implanting a medical device into the body of an afflicted patient. Medical devices may be implanted into the body temporarily or left in the body for extended periods of time, even indefinitely. For example, a surgical mesh may be made from non-biodegradable materials and may be implanted into the abdomen of a patient to repair any type of hernia. The mesh may be either placed over the defect (anterior repair) or under the defect (posterior repair).

In another example, an implantable film made from a bioabsorbable material may be combined with another medical device for delivery of a therapeutic agent. However, these films may include any number of optional ingredients. For instance, viscosity enhancers, emulsifiers, pH modifiers and the like may be added as optional ingredients to the films to enhance the durability of the device and/or alter the delivery characteristics of a therapeutic agent. Typically, optional ingredients represent up to about 10% by weight of the device. In many instances, higher concentrations of optional ingredients may provide detrimental effects to the films overall characteristics. For instance, the addition of a plasticizer in concentrations higher than about 10% often make the film too flexible to be useful as an implantable film.

It would be beneficial to provide an implantable film, alone or in combination with a medical device, capable of providing immediate or sustained release of a therapeutic agent following implantation without compromising the overall characteristics of the films.

SUMMARY

Accordingly, the present disclosure describes implantable medical devices which include at least one polymeric film layer made from a mixture of glycerol and at least one biopolymer, wherein the glycerol and the at least one biopolymer represent a weight ratio ranging from about 3:1 to about 1:3, respectively. In embodiments, the polymeric film layer may include at least one therapeutic agent.

In embodiments, the implantable medical devices described herein may include a medical device having a substrate, at least one polymeric film layer attached to the substrate, the polymeric film layer being made from a mixture of glycerol and at least one biopolymer, wherein the glycerol and the at least one biopolymer represent a weight ratio ranging from about 3:1 to about 1:3, respectively, and at least one therapeutic agent. The polymeric layer may be continuous or discontinuous on the substrate of the device.

Also disclosed are methods of delivery of a therapeutic agent which include implanting a medical device into tissue. The medical device including at least one polymeric film layer made from a mixture of glycerol and at least one biopolymer, wherein the glycerol and the at least one biopolymer represent a weight ratio ranging from about 3:1 to about 1:3, respectively, and, at least one therapeutic agent included in the at least one polymeric film layer.

BRIEF DESCRIPTIONS OF THE DRAWINGS

These and other characteristics of the present invention will be more fully understood by reference to the following detailed description in conjunction with the attached drawings, in which.

Figure 4:
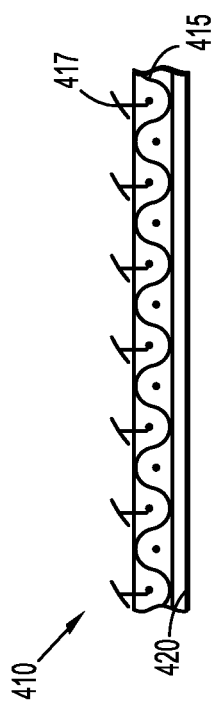
Figure 7:
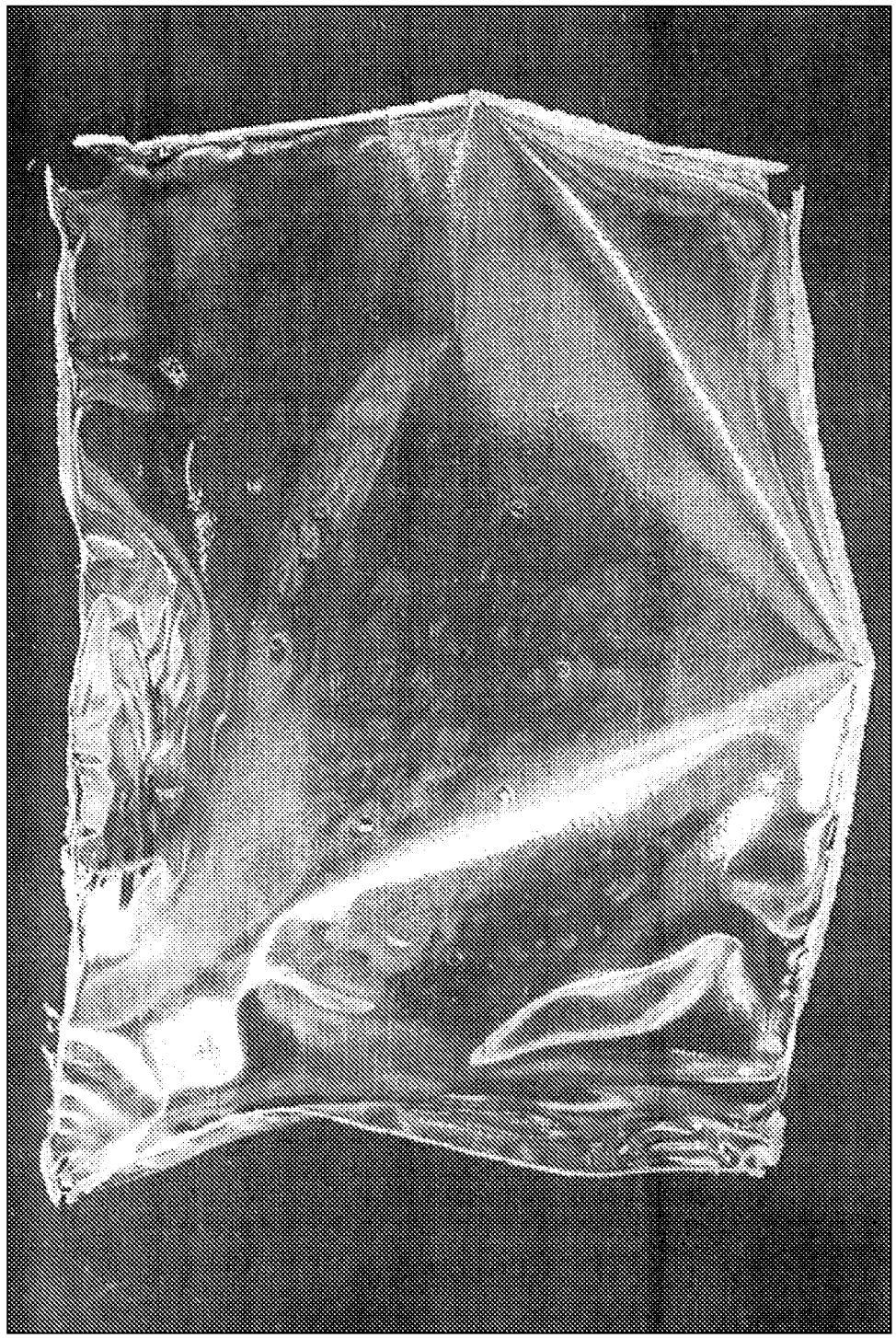
Figure 8:
Figure 9:
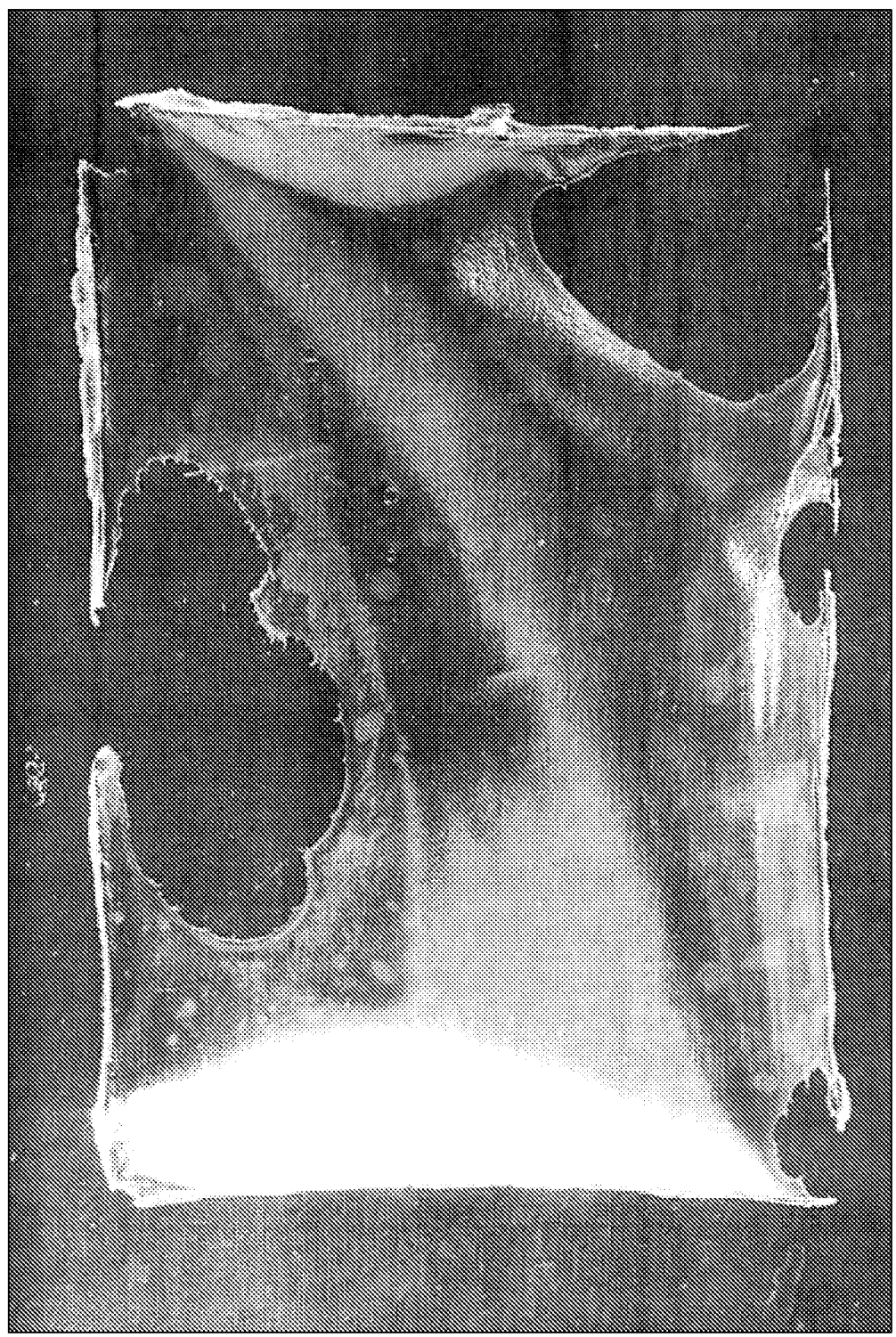
Figure 10:
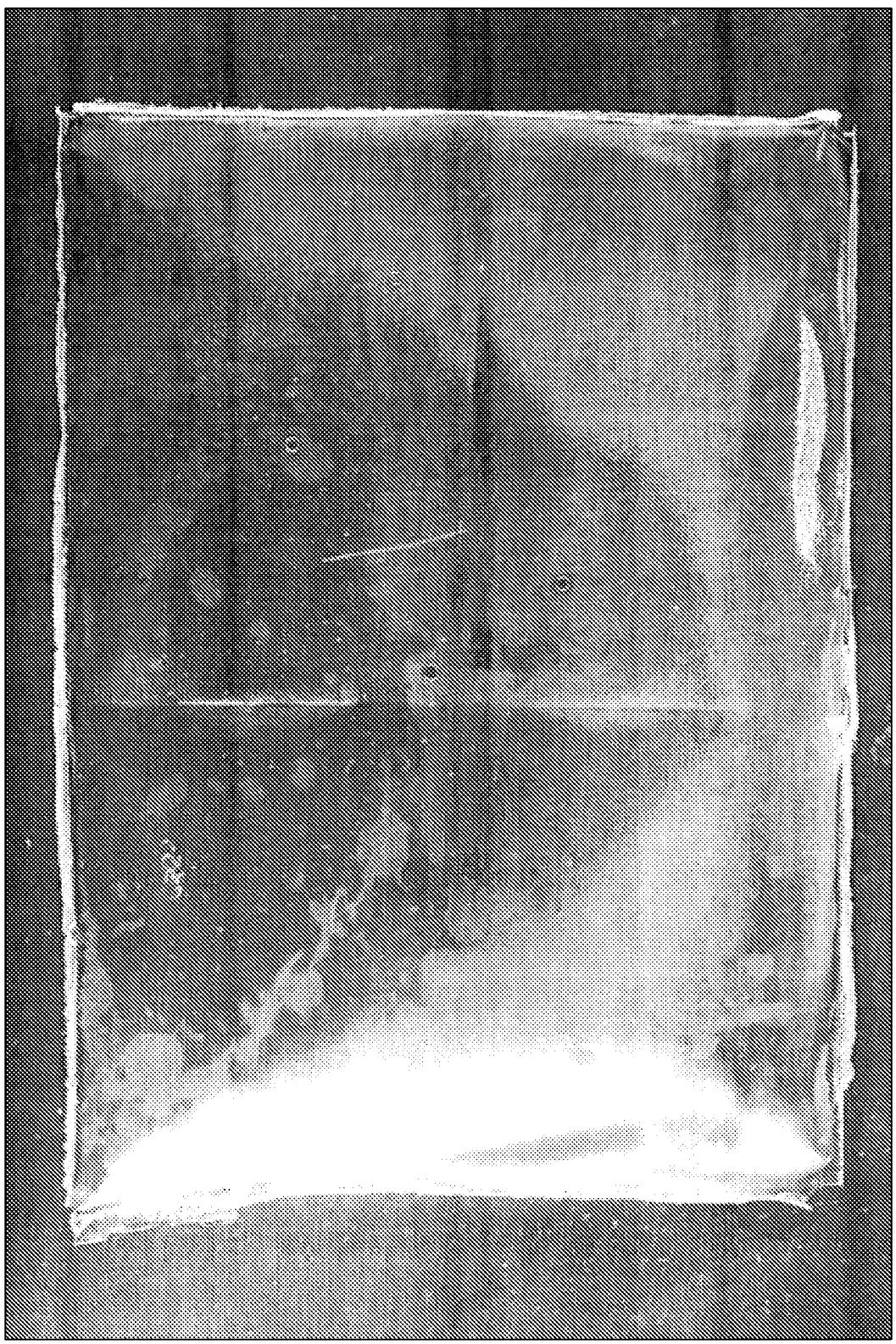
Figure 11:
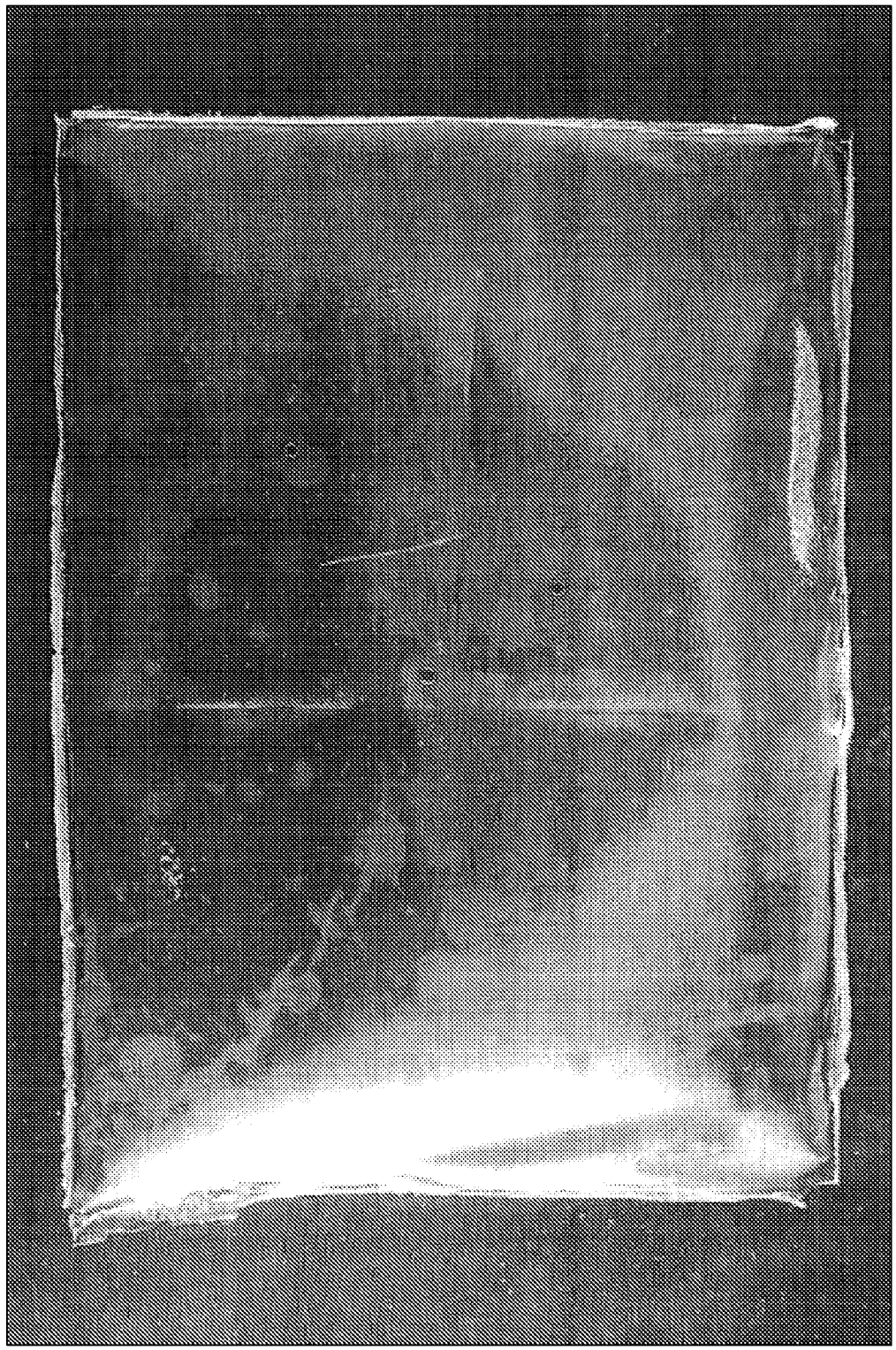
Figure 12:
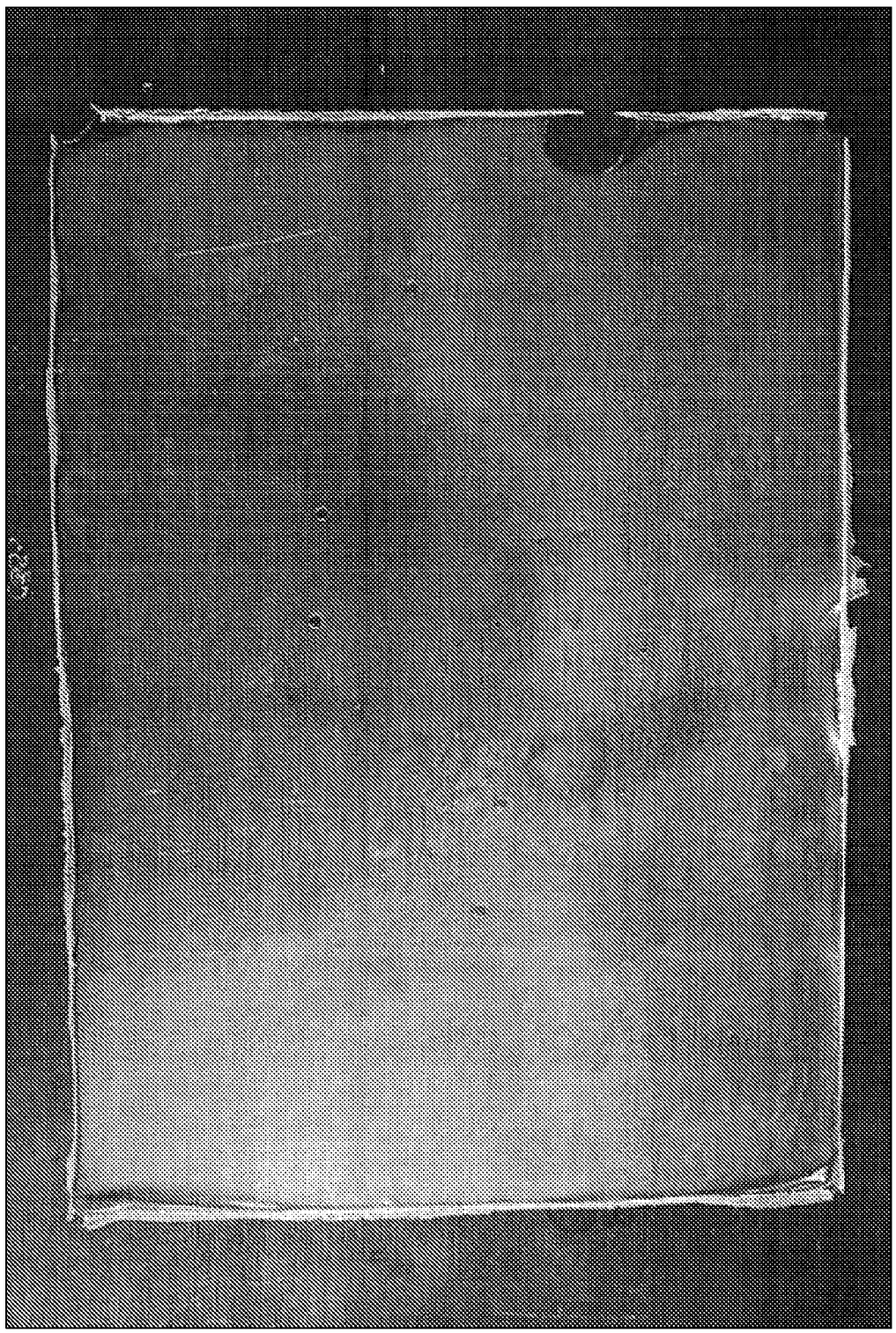
Figure 13:
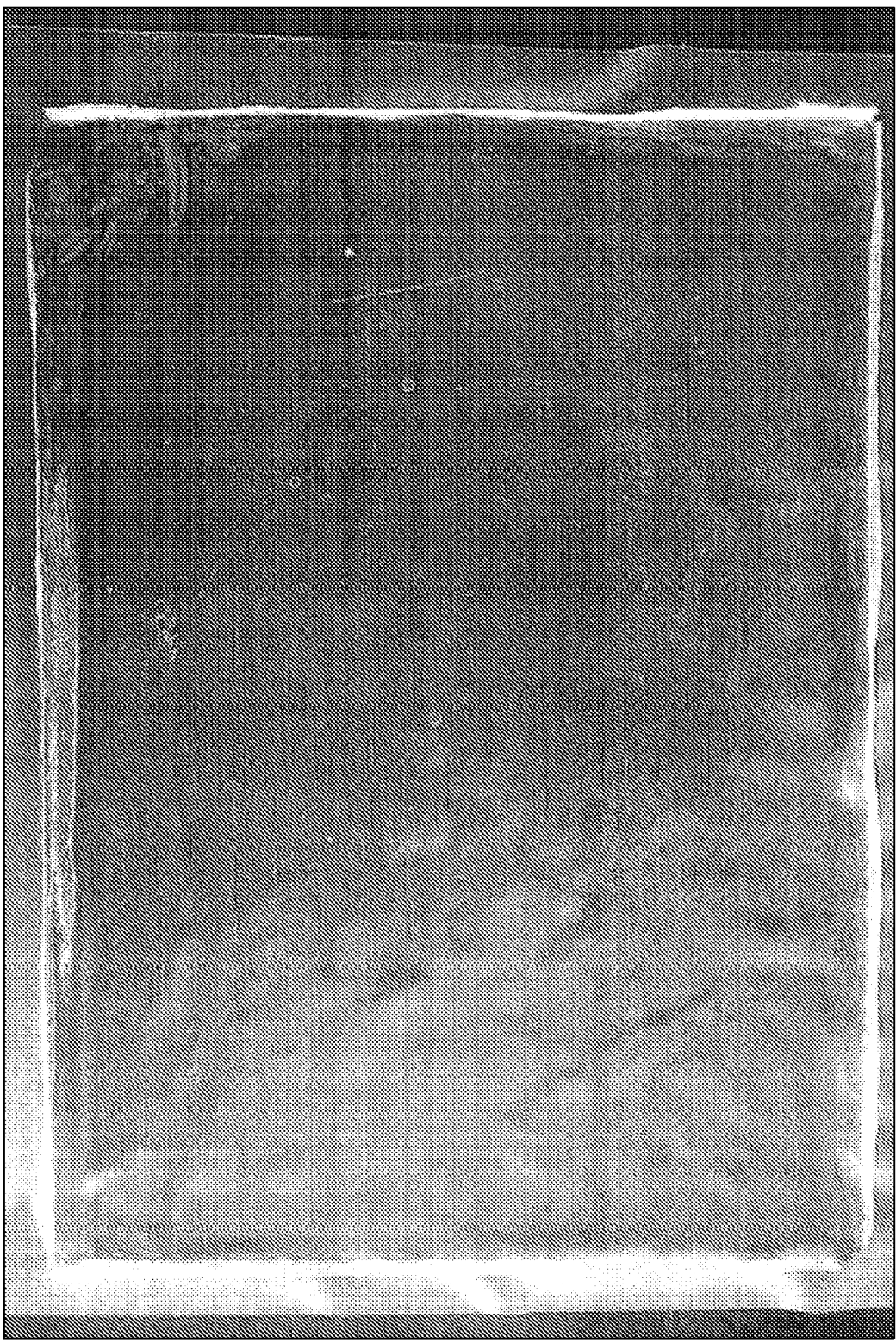
Figure 14:
Figure 15:
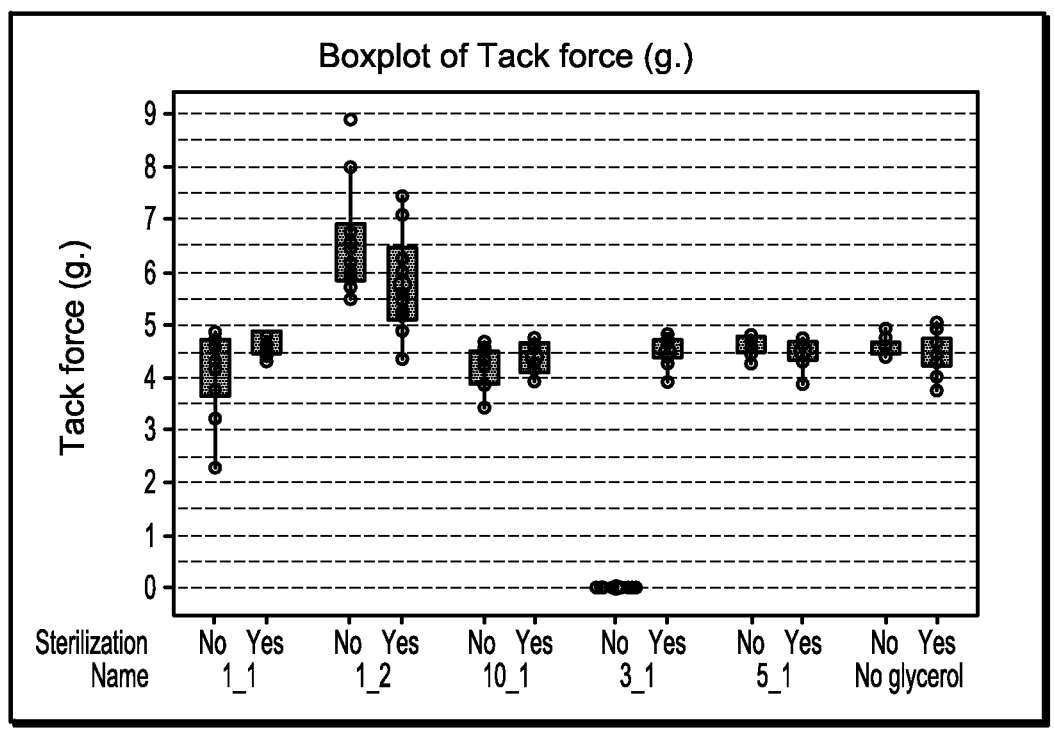
Figure 16:
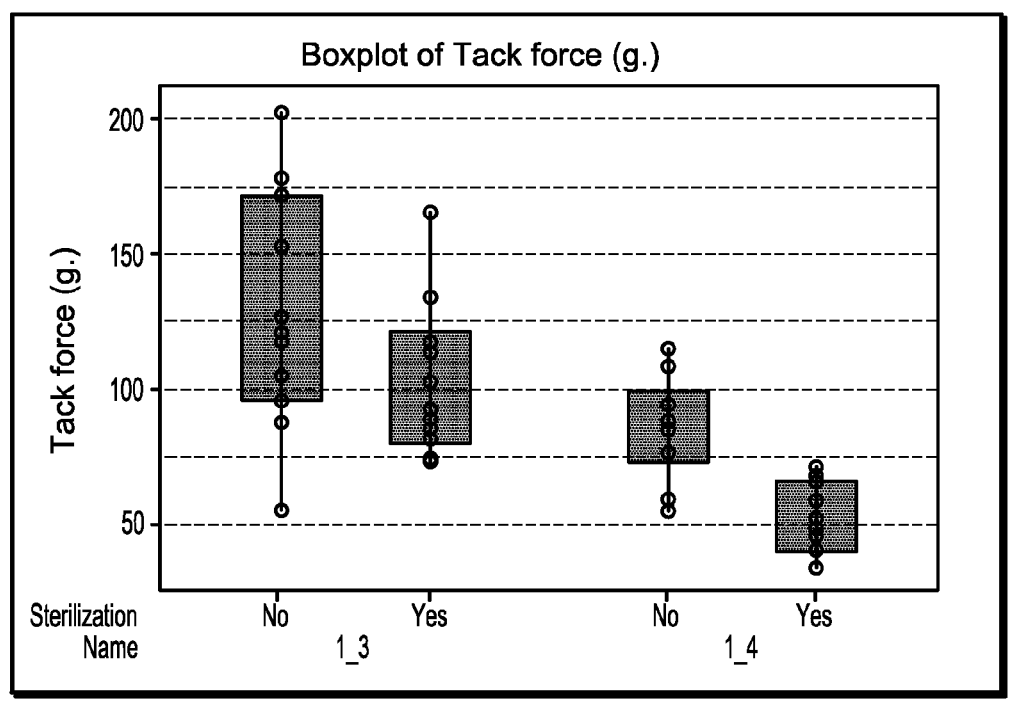
Figure 17:
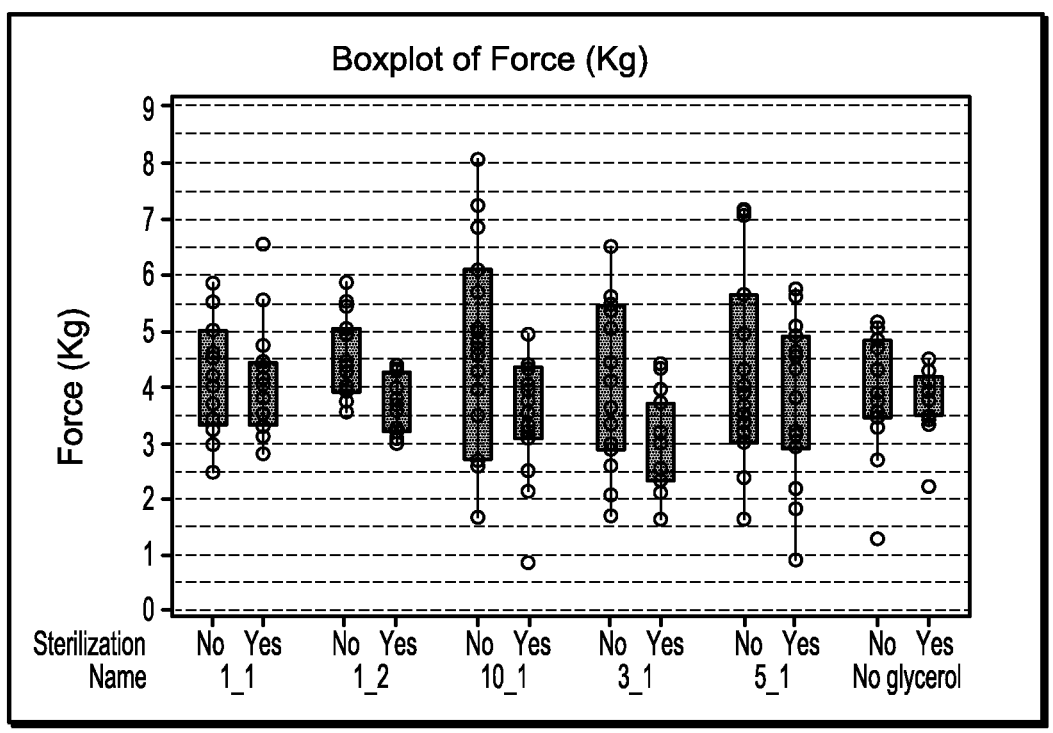
Figure 18:
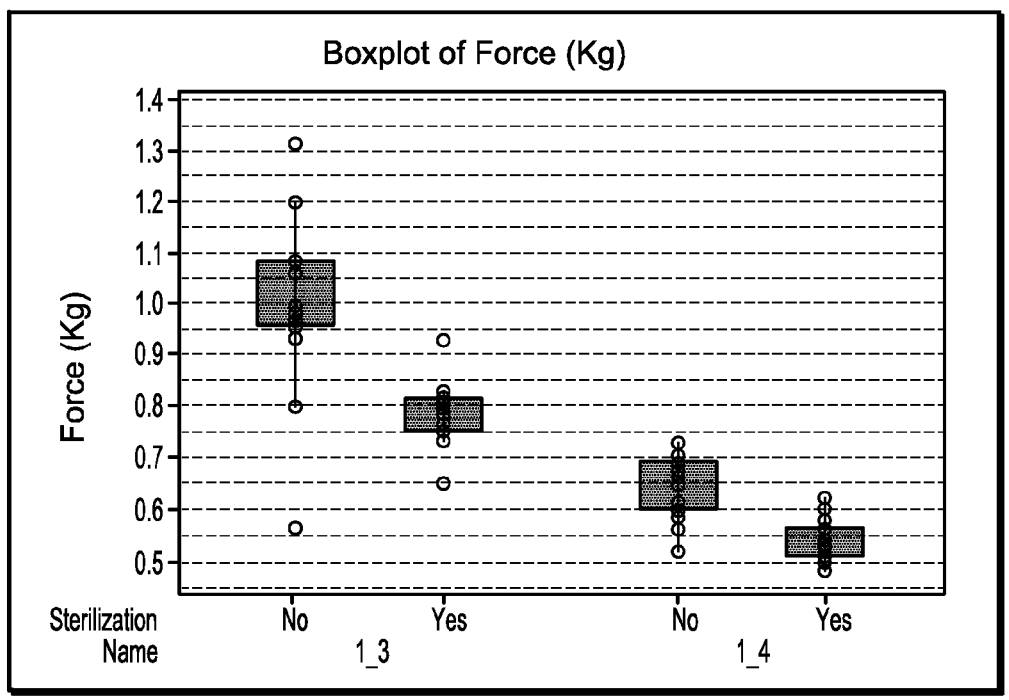
Figure 19:
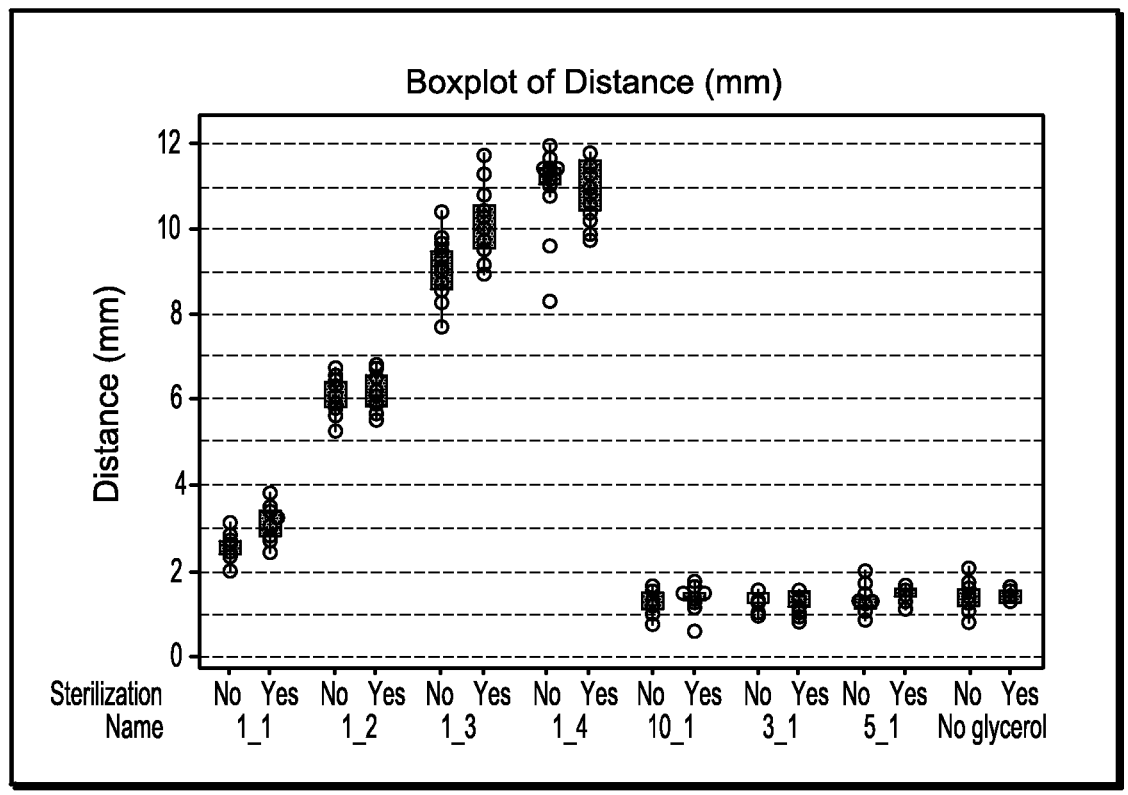

FIGS. 3A, 3B, 3C, 3D, 3E, and 3F are diagrammatic views of the glycerol films in accordance with other embodiments described in the present disclosure;

FIG. 4 is a side view of a medical device according to another embodiment described in the present disclosure;

FIG. 5 is a side view of a medical device according to yet another embodiment described in the present disclosure;

FIG. 6 is a side view of a medical device according to still another embodiment described in the present disclosure;

FIG. 7 is an image of a comparative example of an implantable medical device as described herein;

FIG. 8 is an image of another comparative example of an implantable medical device as described herein;

FIG. 9 is an image of yet another comparative example of an implantable medical device as described herein;

FIG. 10 is an image of an example of an implantable medical device as described herein;

FIG. 11 is an image of another example of an implantable medical device as described herein;

FIG. 12 is an image of yet another example of an implantable medical device as described herein;

FIG. 13 is an image of still another example of an implantable medical device as described herein;

FIG. 14 is an image of another example of an implantable medical device as described herein;

FIG. 15 is a chart displaying tack test results of the implantable medical devices depicted in FIGS. 7-12 as described herein;

FIG. 16 is a chart displaying tack test results of the implantable medical devices depicted in FIGS. 13-14 as described herein;

FIG. 17 is a chart displaying burst test results of the implantable medical devices depicted in FIGS. 7-12 as described herein;

FIG. 18 is a chart displaying burst test results of the implantable medical devices depicted in FIGS. 13-14 as described herein; and FIG. 19 is a chart displaying the distance of displacement results from the burst test of the implantable medical devices depicted in FIGS. 7-14 as described herein.

DETAILED DESCRIPTION

The present disclosure relates to an implantable medical device which includes at least one polymeric film layer made from a mixture of glycerol and at least one biopolymer. The glycerol and the at least one biopolymer represent a weight ratio ranging from about 3:1 to about 1:3, respectively. In some embodiments, glycerol may represent a predominant amount of the polymeric film layer by weight. In some embodiments, the implantable medical device may be used for delivery of at least one therapeutic agent.

By implantable, the medical devices described herein may be positioned, for any duration of time, at a location within a body, such as within a portion of the abdominal cavity. Furthermore, the terms "implantation" and "implanted" refer to the positioning, for any duration of time, of a medical device at a location within a body, such as within a portion of the abdominal cavity.

Glycerol, also known as glycerin or glycerine, is a polyol which includes three hydrophilic hydroxyl groups. The hydroxyl groups allow glycerol to be soluble in water, as well as hygroscopic in nature.

The glycerol may represent from about 25 weight percent to about 75 weight percent of the polymeric film layer. In some embodiments, glycerol may represent from about 33 weight percent to about 67 weight percent of the polymeric film layer. In certain embodiments, the polymeric film layers described herein may include more than 50 weight percent glycerol.

The glycerol used to form the polymeric films described may be in a solid or liquid form prior to mixing with the at least one biopolymer. By solid, the glycerol may be in a form such as particulate, powder, granulized, and the like. By liquid, the glycerol may be in a form such as a solution, suspension, emulsion, dispersion, slurry, gel, and the like.

A glycerol solution maybe formed using any suitable technique within the purview of those skilled in the art. For example, a glycerol solution may be formed by mixing a glycerol solid with a suitable solvent to form a glycerol solution or liquid. Some non-limiting examples of solvents suitable for forming the glycerol solutions may include polar and non-polar solvents such as methylene chloride, chloroform, N-methylpyrrolidone, tetrahydrofuran, dimethylformamide, methanol, ethanol, hexanes, acetone, water, saline buffers and combinations thereof.

The glycerol may be mixed with at least one biopolymer. Some non-limiting examples of suitable biopolymer materials include polysaccharides, proteins, peptides, and combinations thereof. In some embodiments, the polysaccharide may include cellulose, dextran, chitin, chitosan, alginate, pectin, mucilage, pullalan, methylcellulose, carboxymethylcellulose (CMC), hydroxypropyl methylcellulose, hydroxyethyl methylcellulose, arabinoxylans, bacterial polysaccharides and combinations thereof. In certain embodiments, the polymeric film layer may consist of glycerol and carboxymethylcellulose.

In other embodiments, the polymeric film layer may include proteins, such as collagen, elastin, fibrin, albumin, fibrinogen, thrombin, silk, and combinations thereof. In certain embodiments, the polymeric film layer may consist of glycerol and collagen. In other embodiments, the implant has a collagen layer and a carboxymethylcellulose/glycerol layer.

The term "collagen" is meant to include any type of collagen, whether natural or synthetic, of human or animal origin, such as, for example, enriched human collagen of type I, human collagen of type III, also enriched, human collagen of type I+III or of type IV or other collagens such as animal collagen of type I or of type I+III. The collagen may be oxidized or non-oxidized.

In certain embodiments, the collagen may be oxidized without crosslinking. For example, native collagen may be dipped in an acid solution and/or washed, to eliminate the telopeptides, notably by pepsin digestion.

The collagen may also be modified by oxidative cleavage. For this purpose periodic acid or one of its salts can be used, applying the technique described by M. TARDY et al. (FR-A-2 601 371 and U.S. Pat. No. 4,931,546, the entire contents of which are hereby incorporated by reference).

It is recalled briefly that this technique consists of mixing the collagen in acid solution with a solution of periodic acid or one of its salts at a concentration of between 1 and $10^{-5}$M, preferably between $5\ 10^{-3}$ and $10^{-1}$M, at a temperature of between 10 and 25° C. for 10 minutes to 72 hours.

This process breaks down some of the collagen's components, these being hydroxylysine and the sugars, thus creating reactive sites without causing crosslinking.

The oxidative cleavage of collagen allows moderate cross-linking later in the collagenic material but does not exclude the possibility of providing this function by other means of moderate cross-linking, for example by beta or gamma irradiation, or other agents of moderate cross-linking, for example chemical reagents at suitably low and non-toxic doses.

For some applications, the polymer film layers described herein may include collagen which is not oxidized or a mixture in any proportions of non-oxidized and oxidized collagens.

In some embodiments, the biopolymer may represent from about 25 weight percent to about 75 weight percent of the polymeric film layer. In other embodiments, the biopolymer may represent from about 33 weight percent to about 67 weight percent of the polymeric film layer. In certain embodiments, the polymeric film layers described herein may include less than 50 weight percent biopolymer.

The biopolymer used to form the polymeric films described may be in a solid or liquid fowl prior to mixing with the glycerol. By solid, the biopolymer may be in a form such as particulate, powder, granulized, and the like. By liquid, the biopolymer may be in a form such as a solution, suspension, emulsion, dispersion, slurry, gel, and the like.

In particularly useful embodiments, a biopolymer solution maybe formed using any suitable technique within the purview of those skilled in the art. For example, a biopolymer solution may be formed by mixing a biopolymer solid with a suitable solvent to form a biopolymer solution or liquid. For example, carboxymethylcellulose powder may solubilized in water to form a carboxymethylcellulose solution. Some non-limiting examples of solvents suitable for forming the biopolymer solutions may include polar and non-polar solvents, such as methylene chloride, chloroform, N-methylpyrrolidone, tetrahydrofuran, dimethylformamide, methanol, ethanol, hexanes, acetone, water, saline, buffers and combinations thereof.

The polymeric film layers described herein may include glycerol and at least one biopolymer at a weight ratio ranging from about 3:1 to about 1:3. In some embodiments, the glycerol and the biopolymer may represent a weight ratio ranging from about 2:1 to about 1:2. In still other embodiments, the glycerol and the biopolymer may represent a weight ratio greater than about 1.01:1.

Upon mixing of the glycerol and the biopolymer, the polymeric film layers may be formed using any suitable method known to those skilled in the art. Some non-limiting examples include casting, extruding, spraying and the like. In embodiments, the mixture containing the biopolymer and the glycerol may be cast in a mold and allowed to dry to form a polymeric film layer. The drying may take place at an ambient or elevated temperatures and pressures.

The polymeric film layers described herein may be sufficient in strength to be implanted without an additional device for mechanical support. However, in some embodiments, the polymeric film layers described herein may be combined with another implantable substrate, i.e., a mesh, to provide additional support.

Any implantable substrate suitable for insertion into a patient's body, whether on a temporary or a permanent basis, may be combined with the polymeric films described herein. Some non-limiting examples include soft tissue repair devices such as sutures, staples, meshes, patches, pledgets, buttresses, clips, clamps, screws, and pins. Other suitable devices include staple line reinforcements, tissue fillers, tissue wraps for solid organs or luminal structures, sealing devices, cavity wall and floor reinforcements, intramuscular conduits, access site closure devices, and the like. The implantable substrates and the films described herein may be porous or non-porous.

In certain embodiments, the implantable substrate is a surgical mesh. The surgical mesh described herein may include porous fabrics made from intertwined filaments. The filaments may extend horizontally and vertically in a manner which produces sections where the filaments cross-over one another creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. No. 7,021,086, U.S. Pat. No. 6,596,002, U.S. Pat. No. 7,331,199, the entire contents of which are incorporated by reference herein.

The filaments may be monofilaments or multi-filaments and, in embodiments, a plurality of multi-filaments may be combined to form yarns. It is envisioned that the mesh may be configured to any size and/or shape suitable for hernia repair. The filaments may comprise core/sheath constructs.

In certain embodiments, the implantable substrate may be a surgical mesh knitted on a warp knitting machine, of the tricot or Raschel type, with at least three sheets or warps of yarn and as many guide bars.

Figure 1:
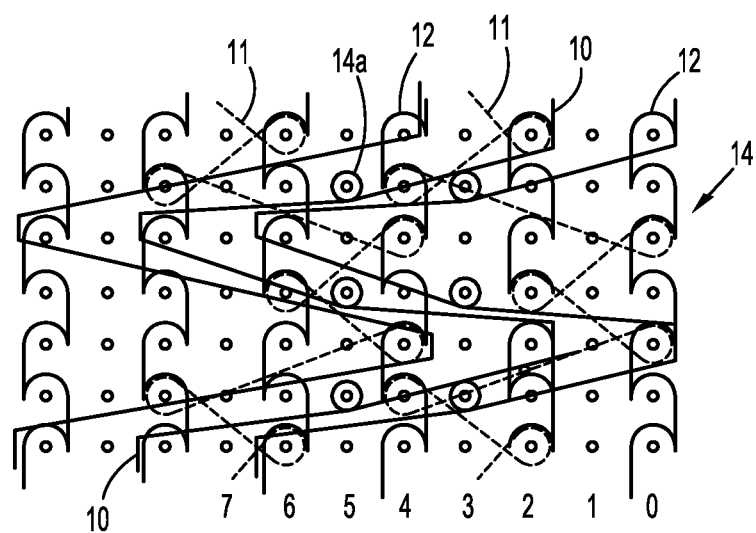
FIG. 1 is a diagram showing the weave of three sheets forming a medical device according to one embodiment described in the present disclosure.

The knitted mesh may be created by threading a rear bar, one guide full and one guide empty, with first mono- or multi-filaments 10 of a biocompatible polymer as represented as a solid line in FIG. 1. An intermediate bar is threaded, one guide full, three guides empty, with second mono- or multi-filaments 11 of a biocompatible polymer as represented as a broken line in FIG. 1. The intermediate bar works in such a way as to obtain a zigzag openwork pattern between the columns of meshes. Finally, a front bar is threaded, one guide full, one guide empty, and works in a chain stitch with third mono- or multi-filaments 12 a biocompatible polymer as represented by a thin line in FIG. 1. The third filament 12, i.e., a chain stitch, imprisons first filament 10 and maintains the length of the mesh while contributing to the formation of the mesh with the intermediate sheet formed by the second filament 11. The different filaments may form yarns and may be worked according to the following chart:

| Warp | | |
|---|---|---|
| Rear bar I | Intermediate bar II Raschel | Front bar III |
| Front bar I | Intermediate bar II | Rear bar III |
| 7 | 3 | 1 |
| 7 | 2 | 0 |
| — | — | — |
| 3 | 4 | 0 |
| 4 | 5 | 1 |
| — | — | — |
| 0 | 1 | |
| 0 | 0 | |

| Warp | | |
|---|---|---|
| Rear bar I | Intermediate bar II Raschel | Front bar III |
| Front bar I | Intermediate bar II | Rear bar III |
| 4 | 2 | |
| 3 | 3 | |
| — | — | |
| | 1 | |
| | 0 | |
| — | — | |
| | 4 | |
| | 5 | |

The rear bar places the first filament or yarn in partial weft under the chain stitch and "thrown" onto the needle not forming a chain stitch. For this reason, at the next row, the needle not forming a chain stitch not being supplied permits escape of the filament which forms a loop 14a projecting from the front face of the mesh.

The threading—one guide full, three guides empty—in the intermediate bar, associated with the displacement, makes it possible to form a light ground texture, stable in width, and open-worked to permit good tissue integration.

The mesh 14 thus obtained may be provided with loops 14a (FIG. 2) which may be perpendicular to one of the mesh surfaces. Loops 14a may also include a rigidity and hold at a right angle which may be obtained by the rigidity or nerve of the filaments employed. This rigidity may be necessary for the subsequent formation of spiked naps which ensure a grip function.

Figure 2:
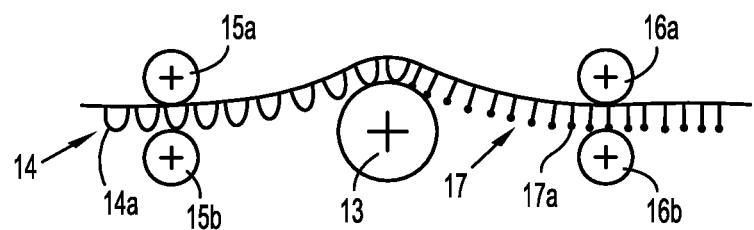
FIG. 2 is a diagrammatic side view of a device permitting the formation of spiked naps on the medical device of FIG. 1 according to another embodiment described in the present disclosure.
Figure 3A:
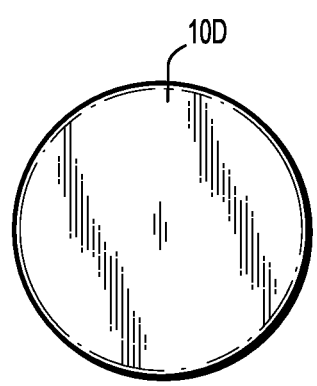
Figure 3B:
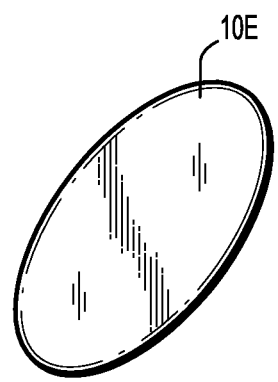
Figure 3C:
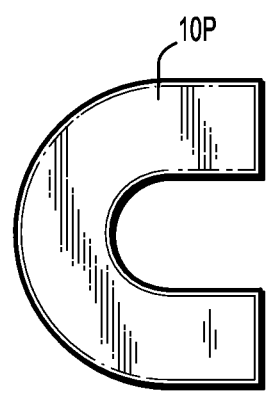
Figure 3D:
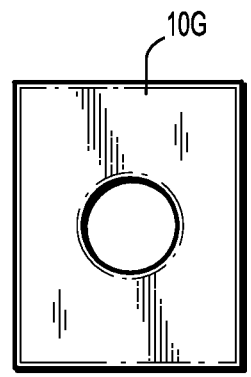
Figure 3E:
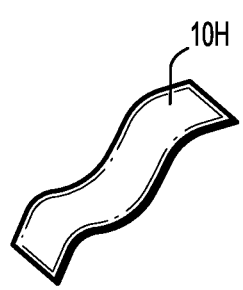
Figure 3F:
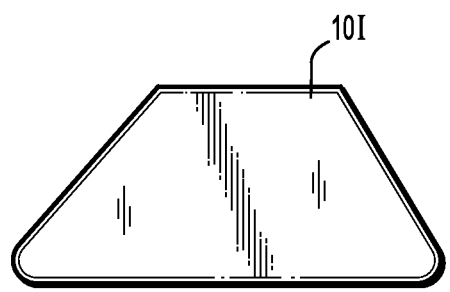

On leaving the loom, mesh 14 may be subjected to a thermosetting operation which stabilizes the mesh length and width. The mesh may then be subjected to a phase of formation of the spiked naps consisting, as is shown in FIG. 2, in passing the mesh over a cylinder 13 containing an electrical heating resistor. Mesh 14 is pressed flat on cylinder 13 by two pairs of rollers, upstream 15a, 15b and downstream 16a, 16b, respectively, which are vertically displaceable for controlling this pressing force.

This control as well as that of the temperature of the resistor placed in cylinder 13 and of the speed of movement of mesh 14 across cylinder 13 make it possible to melt the head of each of loops 14a so that each loop 14a forms two spiked naps 17.

Each spiked nap 17 thus may have a substantially rectilinear body protruding perpendicularly with respect to mesh 14 and, at the free end of this body, a head 17a of greater width than that of the body. Head 17a has a generally spheroidal shape or a mushroom shape. Spiked naps 17 gives mesh 14 the ability to attach to tissue when implanted. In addition, spiked naps 17 may attach to other portions of mesh 14 when folded or rolled.

In embodiments, the polymeric films described herein may be positioned on any portion of the mesh. In some embodiments, the polymeric films may be positioned on a portion of the mesh which does not include the spiked naps. Alternatively, the film may be positioned on a portion of the mesh having spiked naps.

The films may be posited on any portion of the surface of the implantable substrate. In some embodiments, the films may form a continuous layer. For example, the polymeric films may form a continuous layer on the surface of a surgical mesh, wherein the porosity of the mesh is occluded by the continuous film. In other embodiments, the films may form a discontinuous layer covering intermittent portions of the surface of the implantable substrate. In one example, the polymeric films may form a discontinuous layer on the surface of a surgical mesh, wherein the porosity of the mesh is maintained by the discontinuous film.

In some embodiments, the polymeric films may be cast as a film directly on a portion of the implantable substrate surface. In other embodiments, the polymeric films may be spray coated directly on a portion of the implantable substrate surface. In still other embodiments, the polymeric films may be formed before being positioned onto the implantable substrate.

The implantable substrates described herein may be made from any biocompatible material suitable for implantation. For example, the implantable substrate may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1, dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly(ortho esters), hydroxy alkanoates, tyrosine carbonates, polyimide carbonates, polyimino carbonates such as poly(bisphenol A-iminocarbonate) and poly(hydroquinone-iminocarbonate), polyurethanes, polyanhydrides, polymer drugs (e.g., polydiflunisol, polyaspirin, and protein therapeutics) and copolymers and combinations thereof.

In some embodiments, the polymeric films include a single layer containing glycerol, a biopolymer and a therapeutic agent. The thickness of the polymeric films described herein may on average measure between about 0.1 µm to about 1000 µm.

In other embodiments, the polymeric films comprise a multilayer film wherein the first layer contains glycerol and a biopolymer and a second layer contains a therapeutic agent. In still other embodiments, the polymeric films include a tri-layer structure wherein a second layer containing a therapeutic agent is positioned between a first layer containing glycerol and a biopolymer and a third layer containing glycerol and the same or different biopolymer. It is envisioned that the therapeutic agent may also be combined therein any layer of the polymeric films.

The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic affect, such as, antimicrobial agents, anesthetics, analgesics, anticancer agents, angiogenic agents, fibrotic agents, antimitotics, chelating agents, peptides, proteins, DNA, RNA, nucleotides, liposomes, blood products, hormones, water-soluble silver salts, growth factors, antibodies, interleukins, cytokines, and the like. The term "drug' is also intended to include any compound that affects or participates in tissue growth, cell growth, cell differentiation, anti-adhesion of tissue; or a compound that may be able to invoke a biological action such as an immune response; or a compound that could play any other role in one or more biological processes.

Some specific non-limiting examples of water-soluble drugs that may be used in the present self-supporting films include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metofounin, buformin, orotic acid, azathioprine, lactulose, nitrogen mustard, cyclophosphamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof. The water-soluble drug may not need to be converted to a salt form, i.e., tetracycline hydrochloride. In some embodiments, the therapeutic agent may include an anesthetic, i.e., bupivicaine hydrochloride, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with the polymeric film or the implantable substrate. In some embodiments, the therapeutic agent may be a top-coating on the film or implantable substrate to provide an immediate release of the therapeutic agent following implantation. In some embodiments, the therapeutic agent may be included in the film to provide sustained release of the therapeutic agent.

The therapeutic agents may be combined with any suitable solvent to form a therapeutic solution. Some useful non-limiting examples include organic solvents such as methylene chloride, chloroform, N-methylpyrrolidone, tetrahydrofuran, dimethylformamide, methanol, ethanol, hexanes, acetone, water and combinations thereof. In some embodiments, the solvent for the therapeutic agent is not a co-solvent for glycerol or the biopolymer.

The therapeutic agent may form a solution at a concentration ranging from about 1 microgram/ml to about 1 gram/ml. In certain embodiments, the concentration of the therapeutic solution may range from about 1 mg/ml to about 500 mg/ml. In still other embodiments, the concentration of the therapeutic solution may range from about 10 mg/ml to about 300 mg/ml. By solution, the therapeutic preparation is intended to include suspensions, emulsions, dispersions, and the like.

In certain embodiments, the therapeutic agent may be combined with the glycerol and biopolymer mixture prior to the formation of the polymeric film. In such embodiments the glycerol, biopolymer and therapeutic agent may be combined into a solution using a common solvent.

Turning now to FIGS. 3A-3F which illustrate implantable films 10D-10I which contain glycerol and a biopolymer, and optionally a therapeutic agent. Although films 10D-10I are shown as single layer films, multilayer films are also envisioned. Films 10D-10I maintain flexibility to the extent it can be handled without tearing prior to implantation and can adjust to various amounts of force when implanted.

FIGS. 3A through 3F show additional embodiments or configurations of the polymeric films described herein. The embodiments include polymeric film 10D in a circular configuration, polymeric film 10E in an oval configuration, polymeric film 10F in a U-bend configuration, polymeric film 10G in a square configuration having a circular aperture, polymeric film 10H in a wave configuration, and polymeric film 10I in an irregular shape configuration. Each of the configurations of polymeric film 10D through 10I represent different types of configurations. The configurations illustrated are by no means the only possible configurations for polymeric film 10. One of ordinary skill in the art will appreciate that the specific shape or configuration of polymeric film 10 can vary as desired and that the shapes and configurations depicted in FIG. 1 and FIGS. 3A through 3F are illustrative of only a small number of possible shapes and configurations.

In FIG. 4, medical device 410 is a surgical mesh 415 which includes a plurality of spiked naps 417 for grabbing tissue and/or other portions of the mesh. Polymeric film layer 420 is positioned on a portion of surgical mesh 415 which does not include spiked naps 417. However, in embodiments, such as those shown in FIG. 5, polymeric film layer 520 may be positioned on a portion of surgical mesh 515 which includes spiked naps 517.

In still other embodiments, as those shown in FIG. 6, medical device 610 may include more than one polymeric film layer 620a and 620b. Of course, as noted herein, at least one therapeutic agent may be included into any of the medical device, polymeric film layer and combinations thereof for delivery of the therapeutic agent upon implantation.

The implantable substrates and the polymeric films described herein may be formed by combining any combination of individual parts. For example, a polymeric film including glycerol and carboxymethylcellulose may be prepared via solution casting, and a three-dimensional mesh as shown in FIG. 1 may be knit individually. The films may be dried and cut or punched to size and connected to a surface of the mesh via any combination of heat, compression, adhesives, mechanical interlocking, and the like.

In another example, the polymeric film layers and the implantable substrates may be formed together. The surface of the implantable substrates may be put into contact with the polymeric film layers prior to drying to attach the substrate to the polymeric film layer.

In yet another example, the substrate and the multiple polymeric film layers may be formed at the same time as a monolithic structure.

The medical devices described herein may be used to deliver therapeutic agents in the body. The delivery of the agents may be immediate or sustained over time. In embodiments, the polymeric film layer may consist essentially of a predominant amount of glycerol and a minor amount of a biopolymer, such as carboxymethylcellulose or collagen.

EXAMPLES 1-8

Two liters of a 2% medium viscosity carboxymethylcellulose (CMC) stock solution was prepared by mixing 40.0040 grams of CMC with deionized water. The CMC was placed into a two liter volumetric flask with magnetic stirrer and positioned on a magnetic stir plate. The deionized water was slowly added until a 2% CMC stock solution was formed.

The 2% CMC stock solution was mixed with varying amounts of glycerol syrup to form 8 separate 100 ml solutions of the following concentration ratios: 10:1 (CMC:glycerol); 5:1 (CMC:glycerol); 3:1 (CMC:glycerol); 1:1 (CMC:glycerol); 1:2 (CMC:glycerol); 1:3 (CMC:glycerol); 1:4 (CMC:glycerol); and 100% CMC-no glycerol.

Each of the eight CMC:glycerol solutions were then poured into silicone frames positioned on top of silicone sheets on a leveling table. Each of the silicone frames were about 0.5 cm thick and covered an area of about 221 $cm^2$. Each of the silicone frames and the silicone sheets were clamped to the tables prior to the pouring of the CMC:glycerol solutions. The tables were placed into a convection oven set to room temperature and left overnight to dry and form films.

Each of the eight CMC:glycerol films are depicted in FIGS. 7-14. In FIG. 7, a film is shown which contains only CMC and no glycerol. The film was cast from the 2% CMC stock solution as described herein above. The dried film consisting of only CMC was wrinkled and not flat or smooth. The film was brittle and inflexible and when bent would break or crack.

In FIGS. 8 and 9, films formed from a 10:1 mixture of CMC:glycerol and a mixture of 5:1 CMC:glycerol are shown, respectively. Somewhat similar to the film which contained only CMC, the 10:1 CMC:glycerol and the 5:1 CMC:glycerol films dried in a wrinkled or uneven format. The smaller amounts of glycerol, i.e., 10-20% by weight, did not appear to enhance the flexibility of the 10:1 CMC:

glycerol film. Although the 5:1 CMC:glycerol films remained brittle, but when bent did not crack so easily.

The smoothness and flexibility of the films improved as larger amounts of glycerol were added to the films. As shown in FIGS. 10 and 11, films made from a 3:1 mixture of CMC:glycerol and a 1:1 mixture of CMC:glycerol, respectively, are less wrinkled or uneven. In additional the flexibility of the films made from a 3:1 mixture of CMC:glycerol and a 1:1 mixture of CMC:glycerol is also improved making the films easier to handle and less likely to crack.

In FIGS. 12, 13 and 14, films formed from a 1:2 mixture of CMC:glycerol, a mixture of 1:3 CMC:glycerol, and a 1:4 mixture of CMC:glycerol are shown, respectively. The films which include a predominant amount of glycerol appear or foam less-wrinkled or flatter films, as compared to the films with lesser amounts of glycerol than CMC. The elasticity and flexibility of the films in each of FIGS. 11, 12, and 13 is improved by the additional amounts of glycerol as well. In addition, the films containing higher concentrations of glycerol display a tackiness that may be desired upon attachment to a medical device surface or upon attachment to bodily tissue upon implantation. Films formed from a mixture of 1:4 CMC:glycerol displayed a tackiness sufficient to make the film stick to itself when folded over and/or removal from the silicone sheet more difficult.

The 8 films formed of varying concentrations of CMC and glycerol, as depicted in FIGS. 7-14, were each broken down into two groups: sterilized and non-sterilized films. Both groups of films were subjected to Tack testing and Ball Burst Testing.

In the Tack test, the sample films were fixed to a piece of cardboard using double-sided tape. A sample holder was placed over a portion of the film to further secure the samples. A 57R TA probe (made by Texture Technologies Corporation, Scarsdale, N.Y.) was connected a load cell and prompted to approximate the film samples at a rate of 1 mm/sec and applied a force of 30 g for 5 seconds. After contact with the film samples, the probe was retracted from the film samples at a rate of 10 mm/sec. The maximum force of detachment for each group of 8 sample films was recorded.

The results are shown in FIGS. 15 and 16 which display the lower and higher tack forces, respectively. The tack force of the film samples increases in the films wherein glycerol represents a predominant amount of the film.

In the Ball Burst test, the sample films were placed over a TA-108s gel film fixture device (made by made by Texture Technologies Corporation, Scarsdale, N.Y.) and secured in place using a circular plate. A washer with a 9 mm ID was placed in between the film and the circular plate. A 3 mm circular ball probe was connected a load cell and prompted to travel at a compression direction at a rate of 1 mm/sec. The strength and elongation at burst each group of 8 sample films were recorded.

The results are shown in FIGS. 17 and 18 which display the lower and higher burst forces, respectively. As may be noted, the burst force of the film samples increases in the films wherein glycerol represents a predominant amount of the film. In addition, the distance of displacement of each of the film samples at burst was also recorded and the results are depicted in FIG. 19.

It will be understood that various modifications may be made to the embodiments disclosed herein. For example, in embodiments the medical device may be rolled prior to being delivered into the body via a cannula, trocar or laparoscopic delivery device. In another example, the medical devices described herein may be sterilized and packaged into using any suitable sterilization process, i.e., gamma radiation, and any suitable medical device package, i.e., an injectable medical device package. Thus, those skilled in the art will envision other modifications within the scope and spirit of the claims.

What is claimed is:

1. An implantable medical device comprising: a medical device having a substrate, at least one sterile polymeric film layer attached to the substrate, the polymeric film layer consisting of glycerol and carboxymethylcellulose, wherein the glycerol represents more than 50 weight percent of the polymeric film layer and the carboxymethylcellulose represents less than 50 weight percent of the polymeric film layer, wherein the weight percent of the glycerol and the carboxymethylcellulose provides a desired tackiness to promote adhesion of the polymeric film layer and the at least one polymeric film layer is free of hyaluronic acid.

2. The medical device of claim 1, wherein the medical device comprises a surgical mesh.

3. An implantable medical device comprising: at least one sterile polymeric film layer consisting of a mixture of glycerol and carboxymethylcellulose, wherein the glycerol represents more than 50 weight percent of the polymeric film layer and the carboxymethylcellulose represents less than 50 weight percent of the polymeric film layer, wherein the weight percent of the glycerol and the carboxymethylcellulose provides a desired tackiness to promote adhesion of the polymeric film layer and the at least one polymeric film layer is free of hyaluronic acid.

4. The medical device of claim 1, further comprising a collagen layer.

5. The medical device of claim 3, wherein the medical device comprises a surgical mesh.

6. The medical device of claim 3, further comprising a collagen layer.

* * * * *